US012692506B2

(12) United States Patent
Meng et al.

(10) Patent No.: US 12,692,506 B2
(45) Date of Patent: Jul. 28, 2026

(54) RECOMBINANT STRAIN PRODUCING L-LYSINE AND CONSTRUCTION METHODS THEREFOR AND USE THEREOF

(71) Applicant: HEILONGJIANG EPPEN BIOTECH CO., LTD., Daqing (CN)

(72) Inventors: Gang Meng, Daqing (CN); Aiying Wei, Daqing (CN); Huiping Jia, Daqing (CN); Fengyong Ma, Daqing (CN); Xiaoqun Zhou, Daqing (CN); Chunguang Zhao, Daqing (CN); Xiaowei Guo, Daqing (CN); Bin Tian, Daqing (CN); Xiaohang Gao, Daqing (CN)

(73) Assignee: HEILONGJIANG EPPEN BIOTECH CO., LTD., Daqing (CN)

( * ) Notice: Subject to any disclaimer, the term of this patent is extended or adjusted under 35 U.S.C. 154(b) by 654 days.

(21) Appl. No.: 18/001,070

(22) PCT Filed: Dec. 30, 2020

(86) PCT No.: PCT/CN2020/141539
§ 371 (c)(1),
(2) Date: Dec. 7, 2022

(87) PCT Pub. No.: WO2021/248890
PCT Pub. Date: Dec. 16, 2021

(65) Prior Publication Data
US 2023/0295645 A1    Sep. 21, 2023

(30) Foreign Application Priority Data

Jun. 8, 2020    (CN) ......................... 202010514023.X
Aug. 7, 2020    (CN) ......................... 202010790877.0

(51) Int. Cl.
| | |
|---|---|
| *C12N 15/77* | (2006.01) |
| *C07K 14/34* | (2006.01) |
| *C12N 1/00* | (2006.01) |
| *C12N 9/02* | (2006.01) |
| *C12P 13/08* | (2006.01) |

(52) U.S. Cl.
CPC .............. *C12N 15/77* (2013.01); *C07K 14/34* (2013.01); *C12N 1/00* (2013.01); *C12N 9/0004* (2013.01); *C12P 13/08* (2013.01)

(58) Field of Classification Search
None
See application file for complete search history.

(56) References Cited

U.S. PATENT DOCUMENTS

2018/0363014 A1* 12/2018 Voss ........................ C12P 19/30
2020/0095622 A1*  3/2020 Schneider ................ C12N 1/20

FOREIGN PATENT DOCUMENTS

| | | |
|---|---|---|
| CN | 109721658 A | 5/2019 |
| CN | 111197021 A | 5/2020 |
| CN | 111850010 A | 10/2020 |
| CN | 111979165 A | 11/2020 |

OTHER PUBLICATIONS

Accession AAG92219. Jun. 15, 2007 (Year: 2007).*
Accession BX927154. Feb. 27, 2015 (Year: 2015).*
Bornscheuer et al. Curr Protoc Protein Sci. Nov. 2011;Chapter 26:Unit26.7. (Year: 2011).*
Accession Q8NNE7. Oct. 1, 2002 (Year: 2002).*
Accession BX927153. Feb. 27, 2015 (Year: 2015).*
International Search Report and Written Opinion issued in International Application No. PCT/CN2020/141539; mailed Mar. 30, 2021; 17 pgs.
First Office Action issued in Chinese Application No. 202010514023. X; mailed Feb. 4, 2021; 18 pgs.
First Office Action issued in Chinese Application No. 202010790877. 0; mailed Feb. 3, 2021; 14 pgs.
Viability Statement; China General Microbiological Culture Collection Center (CGMCC); CGMCC No. 12856; Aug. 31, 2016; 1 pg.
Notification of Receipt; China General Microbiological Culture Collection Center (CGMCC); CGMCC No. 12856; Aug. 31, 2016; 1 pg.

* cited by examiner

*Primary Examiner* — Christian L Fronda
(74) *Attorney, Agent, or Firm* — HAUPTMAN HAM, LLP

(57)    ABSTRACT

Provided are a method for introducing point mutations to the coding sequence of NCg12176 gene or improving the expression thereof in *Corynebacterium glutamicum*, and a method for performing point mutations on the promoter region sequence of dapB gene in *Corynebacterium glutamicum*. The fermentation yield of L-lysine produced by a strain with the mutations can be increased by means of the methods.

4 Claims, No Drawings

Specification includes a Sequence Listing.

RECOMBINANT STRAIN PRODUCING L-LYSINE AND CONSTRUCTION METHODS THEREFOR AND USE THEREOF

This application is a National Phase of International Application No. PCT/CN2020/141539, filed Dec. 30, 2020, which claims priority to Chinese Patent Application No. 202010790877.0, filed Aug. 7, 2020, and titled "RECOMBINANT STRAIN PRODUCING L-LYSINE AND CONSTRUCTION METHODS THEREFOR AND USE THEREOF"; and Chinese Patent Application No. 202010514023.X, filed Jun. 8, 2020, and titled "DAPB GENE MODIFIED RECOMBINANT STRAIN AND CONSTRUCTION METHODS THEREFOR AND USE THEREOF"; both of which applications are incorporated herein by reference in their entirety.

INCORPORATION BY REFERENCE

The sequence listing provided in the file entitled SQL_PUS1221615_v1.txt, which is an ASCII text file that was created on Dec. 5, 2022, and which comprises 15,631 bytes, is hereby incorporated by reference in its entirety.

TECHNICAL FIELD

The invention belongs to the technical fields of genetic engineering and microorganisms, and relates to a recombinant strain with enhanced L-lysine production capacity, and construction methods therefor and use thereof.

BACKGROUND OF THE INVENTION

L-lysine has physiological functions such as promoting development, enhancing immunity and improving the function of central nervous tissue. It is one of the eight essential amino acids that humans and animals cannot synthesize by themselves and are necessary for growth. Currently, L-lysine is the second largest amino acid variety in the world, and is produced mainly by fermentation. *Corynebacterium* is the most important strain used in amino acid production, including *Corynebacterium glutamicum, C. flavum, C. crenalum, Corynebacterium pekinense*, etc. Among them, *Corynebacterium glutamicum* is an important lysine producing-strain. About 90% of the industrial output of L-lysine is used as a nutrition enhancer in the feed industry, and 10% is used as a flavoring agent and sweetener in the food industry, as well as a pharmaceutical intermediate in the pharmaceutical industry.

Improvements to the fermentation methods for producing L-lysine may involve fermentation techniques such as stirring and supply of oxygen; or involve the composition of the nutrient medium, such as the sugar concentration during fermentation; or involve the processing of a fermentation broth into a suitable product form, such as by drying and pelleting the fermentation broth or by ion exchange chromatography; or may involve the inherent performances and properties of relevant microorganisms.

Methods for improving the performances and properties of these microorganisms include mutagenesis, selection and screening of mutants. Strains obtained in this way are resistant to metabolites or are auxotrophic for metabolites of regulatory importance and can produce L-lysine.

Taking *Corynebacterium glutamicum* as an example, 4 mol of NADPH is required to synthesize 1 mol of L-lysine in the biosynthetic pathway in *C. glutamicum*. Therefore, in order to increase the accumulation of L-lysine in the biosynthetic pathway in *C. glutamicum*, it is a very important strategy to increase the amount of NADPH in the metabolic pathway in *C. glutamicum* or reduce the amount of NADPH required in the L-lysine synthetic pathway.

Dihydrodipicolinate reductase (DHDPR) is the second key enzyme in the biosynthesis of diaminopimelic acid and L-lysine in bacteria and higher plants and catalyze the NAD(P)H-dependent reductive reaction of dihydrodipicolinate to generate hexahydrodipicolinate. This enzyme plays a pivotal role in cell wall formation. DHDPR uses either NADH or NADPH as a cofactor. DHDPRs of different bacteria have different affinities for different cofactors. For example, *E. coli* DHDPR prefers NADH, while *C. glutamicum* DHDPR mainly uses NADPH as a cofactor to participate in the synthesis of L-lysine. Like DHDPRs discovered in other organisms, *C. glutamicum* DHDPR is encoded by the gene dapB, and its enzymatic activity is not regulated by end products in the synthetic pathway but is inhibited by 2,6-pyridinedicarboxylic acid (2,6-PDC).

Lysine yield is related to enzyme activity in the biosynthetic pathway, which can generally be enhanced by amplifying one or more genes in the lysine biosynthetic pathway or by applying modified promoters to genes.

SUMMARY OF THE INVENTION

The invention provides a L-lysine-producing microorganism or recombinant strain, wherein the expression of a polynucleotide encoding the amino acid sequence of SEQ ID NO: 3 is improved, and/or, the bases at positions −49, −51 and −54 to −58 in the promoter region shown in SEQ ID NO: 29 are mutated. The invention also provides a method for producing L-lysine by using the microorganism or recombinant strain.

In a first aspect, the invention provides a L-lysine-producing microorganism or recombinant strain belonging to the genus *Corynebacterium*, which has improved expression of a polynucleotide encoding the amino acid sequence of SEQ ID NO: 3. According to the invention, the improved expression refers to that the expression of the polynucleotide is enhanced, or the polynucleotide encoding the amino acid sequence of SEQ ID NO: 3 has a point mutation, or the polynucleotide encoding the amino acid sequence of SEQ ID NO: 3 has a point mutation and enhanced expression.

The amino acid sequence of SEQ ID NO: 3 is the amino acid sequence of the protein encoded by gene NCgl2176.

Compared to the wild-type or parental strain, the microorganism or recombinant strain has enhanced L-lysine production capacity.

The polynucleotide can encode an amino acid sequence having about 90% or higher, about 92% or higher, about 95% or higher, about 97% or higher, about 98% or higher, about 99% or higher sequence homology with the amino acid sequence of SEQ ID NO: 3. As used herein, the term "homology" refers to the percent identity between two polynucleotides or two polypeptide modules. Sequence homology between one module and another can be determined by methods known in the art. For example, such sequence homology can be determined by BLAST algorithm.

The expression of the polynucleotide can be enhanced by substituting or mutating an expression-regulating sequence, introducing a mutation into the polynucleotide sequence, increasing the copy number of the polynucleotide via chromosomal inclusion or vector introduction, or a combination thereof, and the like.

The expression-regulating sequence of the polynucleotide can be modified. The expression-regulating sequence controls the expression of the polynucleotide to which they are operably linked, and can include a promoter, a terminator, an enhancer, a silencer, etc. The polynucleotide can have a change in the start codon. The polynucleotide can be incorporated into a chromosome at a specific site, thereby increasing copy number. In the invention, the specific site includes a transposon site, an intergenic site, etc. Besides, the polynucleotide can be incorporated into an expression vector and then the expression vector is introduced into a host cell, thereby increasing copy number.

In one embodiment of the invention, the polynucleotide or the point-mutated polynucleotide is incorporated into a chromosome of the microorganism at a specific site, thereby increasing copy number.

In one embodiment of the invention, the polynucleotide carrying a promoter sequence or the point-mutated polynucleotide carrying a promoter sequence is incorporated into a chromosome of the microorganism at a specific site, thereby overexpressing the nucleic acid sequence.

In one embodiment of the invention, the polynucleotide or the point-mutated polynucleotide is incorporated into an expression vector and then the expression vector is introduced into a host cell, thereby increasing copy number.

In one embodiment of the invention, the polynucleotide carrying a promoter sequence or the point-mutated polynucleotide carrying a promoter sequence is incorporated into an expression vector, and then the expression vector is introduced into a host cell, thereby overexpressing the nucleic acid sequence.

In a specific embodiment of the invention, the polynucleotide can comprise the nucleotide sequence of SEQ ID NO: 1.

In one embodiment of the invention, the polynucleotide encoding the amino acid sequence of SEQ ID NO: 3 has a point mutation such that the lysine residue at position 176 of the amino acid sequence of SEQ ID NO: 3 is substituted with a different amino acid residue.

According to the invention, it is preferred that the lysine residue at position 176 is substituted with an asparagine residue.

According to the invention, the amino acid sequence after the lysine (K) residue at position 176 of the amino acid sequence shown in SEQ ID NO: 3 is substituted with an asparagine (N) residue is shown in SEQ ID NO: 4.

In one embodiment of the invention, the point-mutated polynucleotide sequence is formed by the mutation of the base at position 528 of the polynucleotide sequence shown in SEQ ID NO: 1.

According to the invention, the mutation includes base mutation of adenine (A) to cytosine (C) at position 528 of the polynucleotide sequence shown in SEQ ID NO: 1.

In one embodiment of the invention, the point-mutated polynucleotide sequence comprises the polynucleotide sequence shown in SEQ ID NO: 2.

As used herein, the term "operably linked" refers to a functional linkage between a regulatory sequence and a polynucleotide sequence, whereby the regulatory sequence controls the transcription and/or translation of the polynucleotide sequence. The regulatory sequence can be a strong promoter capable of increasing the expression level of the polynucleotide. The regulatory sequence can be a promoter derived from microorganisms belonging to the genus *Corynebacterium* or can be a promoter derived from other microorganisms. For example, the promoter can be a trc promoter, a gap promoter, a tac promoter, a T7 promoter, a lac promoter, a trp promoter, an araBAD promoter or a cj7 promoter.

In a specific embodiment of the invention, the promoter is the promoter of the polynucleotide (NCg12176 gene) encoding the amino acid sequence of SEQ ID NO: 3.

As used herein, the term "vector" refers to a polynucleotide construct that contains a gene sequence and its regulatory sequence and is configured to express the target gene in a suitable host cell. Alternatively, the vector may refer to a polynucleotide construct comprising sequences useful for homologous recombination, whereby the regulatory sequence of the endogenous gene in the genome of the host cell may be altered or the target gene that can be expressed is incorporated into a specific site in the host's genome after the vector is introduced into the host cell. In this regard, the vector used in the invention may further comprise a selectable marker to determine the introduction of the vector into the host cell or the incorporation of the vector into the chromosome of the host cell. The selectable marker can include the marker that confer a selectable phenotype such as drug resistance, auxotroph, cytotoxic agent resistance, or expression of surface proteins. In the context of using such selective agents, transformed cells can be selected because only cells expressing the selectable marker can survive or display different phenotypic traits.

In some specific embodiments of the invention, the vector used is pK18mobsacB plasmid or pXMJ19 plasmid.

As used herein, the term "transformation" refers to the introduction of a polynucleotide into a host cell such that the polynucleotide is replicable as an extra-genomic element or as an element incorporated into the genome of the host cell. The method of transforming the vector used in the invention can include a method of introducing the nucleic acid molecule into the cell. In addition, as disclosed in the related art, the electric pulse method can be employed according to the host cell.

According to the invention, the microorganism or recombinant strain belonging to the genus *Corynebacterium* can be *Corynebacterium glutamicum, Brevibacterium flavum, Brevibacterium lactofermentum, Corynebacterium ammoniagenes, Corynebacterium pekinense.*

In one embodiment of the invention, the microorganism belonging to the genus *Corynebacterium* is *Corynebacterium glutamicum* YP97158, which was deposited on Aug. 16, 2016 at China General Microbiological Culture Collection Center (Address: No. 1 West Beichen Road, Chaoyang District, Beijing, Telephone: 010-64807355) with a deposition number of CGMCC No. 12856 and has been recorded in Chinese Patent Application CN106367432A (Filing date: Sep. 1, 2016; Publication date: Feb. 1, 2017).

According to the invention, the microorganism or recombinant strain can also have other improvements related to increased L-lysine production, for example, increasing or decreasing expression of genes related to NADPH production (such as the gene encoding glucose dehydrogenase, the gene encoding gluconate kinase, the gene encoding glyceraldehyde-3-phosphate dehydrogenase, the gene encoding glucose-6-phosphate dehydrogenase, or the gene encoding 6-phosphogluconate dehydrogenase) and/or other genes involved in biosynthesis or secretion of L-lysine (such as the gene encoding aspartate aminotransferase, the gene encoding aspartate kinase, the gene encoding aspartate semialdehyde dehydrogenase, the gene encoding dihydrodipicolinate synthase, the gene encoding dihydrodipicolinate reductase, the gene encoding m-diaminopimelate dehydrogenase, the gene encoding diaminopimelate decarboxylase, lysE), or substituting a genes with a foreign gene.

In a second aspect, the invention provides a polynucleotide sequence, an amino acid sequence encoded by the polynucleotide sequence, a recombinant vector comprising the polynucleotide sequence, and a recombinant strain containing the polynucleotide sequence.

According to the invention, the polynucleotide sequence comprises a polynucleotide encoding a peptide comprising the amino acid sequence of SEQ ID NO: 3, wherein the lysine residue at position 176 is substituted with a different amino acid residue.

According to the invention, it is preferred that the lysine residue at position 176 is substituted with an asparagine residue.

According to the invention, the amino acid sequence after the lysine (K) residue at position 176 of the amino acid sequence shown in SEQ ID NO: 3 is substituted with an asparagine (N) residue is shown in SEQ ID NO: 4.

According to the invention, it is preferred that the polynucleotide sequence encoding a polypeptide comprising the amino acid sequence shown in SEQ ID NO: 3 comprises the polynucleotide sequence shown in SEQ ID NO: 1.

In one embodiment of the invention, the polynucleotide sequence is formed by the mutation of the nucleotide at position 528 of the polynucleotide sequence shown in SEQ ID NO: 1.

According to the invention, the mutation refers to the change of the base/nucleotide of the site, and the mutation method can be selected from at least one selected from mutagenesis, PCR site-directed mutagenesis and homologous recombination methods. In the invention, preferably, PCR site-directed mutagenesis and/or homologous recombination are used.

According to the invention, the mutation includes base mutation of adenine (A) to cytosine (C) at position 528 of the polynucleotide sequence shown in SEQ ID NO: 1.

In one embodiment of the invention, the polynucleotide sequence comprises the polynucleotide sequence shown in SEQ ID NO: 2.

According to the invention, the amino acid sequence comprises the amino acid sequence shown in SEQ ID NO: 4.

According to the invention, the recombinant vector is constructed by introducing the polynucleotide sequence into a plasmid.

In one embodiment of the invention, the plasmid is pK18mobsacB plasmid.

In another embodiment of the invention, the plasmid is pXMJ19 plasmid.

Specifically, the polynucleotide sequence and the plasmid can be constructed into a recombinant vector via NEBuider recombination system.

According to the invention, the recombinant strain contains the polynucleotide sequence.

As one embodiment of the invention, the starting strain of the recombinant strain is YP97158.

In a third aspect, the invention also provides a construction method of a recombinant strain of *Corynebacterium glutamicum*.

According to the invention, the construction method comprises the step of:
  modifying the polynucleotide sequence of wild-type NCg12176 gene as shown in SEQ ID NO: 1 in a host strain to mutate the base at position 528, thereby obtaining a recombinant strain of genus *Corynebacterium* containing the mutated NCg12176 encoding gene.

According to the construction method of the invention, the modification method can be at least one selected from mutagenesis, PCR site-directed mutagenesis and homologous recombination methods.

According to the construction method of the invention, the mutation refers to the mutation of adenine (A) to cytosine (C) at position 528 of SEQ ID NO: 1; specifically, the polynucleotide sequence comprises the mutated NCg12176 encoding gene is shown in SEQ ID NO: 2.

Further, the construction method comprises the following steps:
  (1) modifying the polynucleotide sequence of wild-type NCg12176 gene as shown in SEQ ID NO: 1 to mutate the nucleotide at position 528, thereby obtaining the polynucleotide sequence of mutated NCg12176 gene;
  (2) ligating the mutated polynucleotide sequence with a plasmid to construct a recombinant vector;
  (3) introducing the recombinant vector into a host strain, thereby obtaining a recombinant *Corynebacterium* strain containing the mutated NCg12176 encoding gene.

According to the construction method of the invention, step (1) comprises the step of constructing point-mutated NCg12176 gene: according to the genomic sequence of *Corynebacterium glutamicum*, synthesizing two primer pairs, P1 and P2, and P3 and P4, for amplifying the NCg12176 gene fragment, introducing a point mutation into the wild-type NCg12176 gene as shown in SEQ ID NO: 1 by PCR site-directed mutagenesis, thereby obtaining the point-mutated NCg12176 gene having the nucleic acid sequence of SEQ ID NO: 2, which is denoted as NCg12176$^{A528C}$.

In one embodiment of the invention, the genome of *Corynebacterium glutamicum* can be derived from ATCC13032 strain, the genomic sequence of which is available from the NCBI website.

In one embodiment of the invention, in step (1), the primers are as follows:

```
P1:
                              (SEQ ID NO: 5)
5' CAGTGCCAAGCTTGCATGCCTGCAGGTCGACTCTAGCGGCGACCGC
ATGGACACCG 3'

P2:
                              (SEQ ID NO: 6)
5' CCGGGGACTGGTTTTCGGGTGTTGGTGTGC 3'

P3:
                              (SEQ ID NO: 7)
5' GCACACCAACACCCGAAAACCAGTCCCCGG 3'

P4:
                              (SEQ ID NO: 8)
5' CAGCTATGACCATGATTACGAATTCGAGCTCGGTACCCCGAGGTCT
CTCAGAATCGGT 3'
```

In one embodiment of the invention, the PCR amplification procedure is as follows: 30 cycles of denaturation at 94° C. for 30 s, annealing at 52° C. for 30 s, and extension at 72° C. for 40 s.

In one embodiment of the invention, the overlap PCR amplification procedure is as follows: 30 cycles of denaturation at 94° C. for 30 s, annealing at 52° C. for 30 s, and extension at 72° C. for 90 s.

According to the construction method of the invention, step (2) comprises the step of constructing a recombinant plasmid, comprising: assembling the isolated and purified NCg12176$^{A528C}$ and pK18mobsacB plasmid via NEBuider recombinant system to obtain a recombinant plasmid pK18-NCg12176$^{A528C}$.

According to the construction method of the invention, step (3) comprises the step of constructing a recombinant strain, comprising: transforming the recombinant plasmid pK18-NCg12176$^{A528C}$ into a host strain, thereby obtaining a recombinant strain.

In one embodiment of the invention, the transformation method in step (3) is electro-transformation method.

In one embodiment of the invention, the host strain is YP97158.

In one embodiment of the invention, the recombination is achieved by homologous recombination.

In a fourth aspect, the invention also provides a construction method of a recombinant *Corynebacterium* strain.

According to the invention, the construction method comprises the following steps:

amplifying the upstream and downstream homologous arm fragments of the NCg12176 gene, the NCg12176 gene coding region and its promoter region sequence, or, the NCg12176$^{A528C}$ gene coding region and its promoter region sequence, and introducing the NCg12176 or NCg12176$^{A528C}$ gene into the genome of a host strain by homologous recombination to realize the overexpression of NCg12176 or NCg12176 A528C gene in the strain.

In one embodiment of the invention, primers for amplifying the upstream homologous arm fragment are as follows:

```
P7:
                                    (SEQ ID NO: 11)
5'CAGTGCCAAGCTTGCATGCCTGCAGGTCGACTCTAGAATGCGTTCTG
GACTGAGG3'

P8:
                                    (SEQ ID NO: 12)
5'AACACCATTGTCCCTGTTTTGGGCGAAATTTTCCCGGTGCACCGAGA
ACAGATG3'.
```

In one embodiment of the invention, primers for amplifying the downstream homologous arm fragment are as follows:

```
P11:
                                    (SEQ ID NO: 15)
5'CTACGAGACGAAGCCGTTCGCCTGAGATGGCGCAATTAAATCAAG
3'

P12:
                                    (SEQ ID NO: 16)
5'CAGCTATGACCATGATTACGAATTCGAGCTCGGTACCCGCTATGACA
CCTTCAACGGATC 3'.
```

In one embodiment of the invention, primers for amplifying the gene coding region and its promoter region sequence are as follows:

```
P9:
                                    (SEQ ID NO: 13)
5'CGGGAAAATTTCGCCCAAAACAGGGACAATGGTGTTATGGCATTTGC
AGACATTGTGCGC3'

P10:
                                    (SEQ ID NO:14)
5'CTTGATTTAATTGCGCCATCTCAGGCGAACGGCTTCGTCTCGTAG3'.
```

In one embodiment of the invention, using above P7 and P12 as primers and the mixed three fragments of the upstream homologous fragment, the downstream homologous fragment and the NCg12176 or NCg12176$^{A528C}$ gene with its own promoter as the template, PCR was performed to obtain an integrating homologous arm fragment.

In one embodiment of the invention, the PCR system used is as follows: 10×Ex Taq Buffer 5 µL, dNTP Mixture (2.5 mM each) 4 µL, Mg$^{2+}$ (25 mM) 4 µL, primers (10 pM) 2 µL each, Ex Taq (5 U/µL) 0.25 µL, total volume 50 µL; the PCR amplification procedure is as follows: initial denaturation at 94° C. for 5 min; 30 cycles of denaturation at 94° C. for 30 s, annealing at 52° C. for 30 s, and extension at 72° C. for 120 s; and a final extension at 72° C. for 10 min.

In one embodiment of the invention, NEBuider recombination system is used to assemble the shuttle plasmid PK18mobsacB and the integrating homologous arm fragment to obtain an integrating plasmid.

In one embodiment of the invention, the integrating plasmid is transfected into a host strain, and the NCg12176 or NCg12176$^{A528C}$ gene is introduced into the genome of the host strain by homologous recombination.

In one embodiment of the invention, the host strain is YP97158.

In one embodiment of the invention, the host strain is a strain carrying the polynucleotide sequence shown in SEQ ID NO: 2.

In a fifth aspect, the invention also provides a construction method of a recombinant *Corynebacterium* strain.

According to the invention, the construction method comprises the following steps:

amplifying the NCg12176 gene coding region and its promoter region sequence, or the NCg12176$^{A528C}$ gene coding region and its promoter region sequence, constructing an overexpression plasmid vector, and introducing the vector into a host strain to realize the overexpression of NCg12176 or NCg12176$^{A528C}$ gene in the strain.

In one embodiment of the invention, primers for amplifying the gene coding region and its promoter region sequence are as follows:

```
P17:
                                    (SEQ ID NO: 21)
5'GCTTGCATGCCTGCAGGTCGACTCTAGAGGATCCCCCGGGAAAATTT
CGCCCAAAACAG3',

P18:
                                    (SEQ ID NO: 22)
5'ATCAGGCTGAAAATCTTCTCTCATCCGCCAAAACTCAGGCGAACGGC
TTCGTCTCGTAG 3'.
```

In one embodiment of the invention, the PCR system is as follows: 10×Ex Taq Buffer 5 µL, dNTP Mixture (2.5 mM each) 4 µL, Mg$^{2+}$ (25 mM) 4 µL, primers (10 pM) 2 µL each, Ex Taq (5 U/µL) 0.25 µL, total volume 50 µL; the PCR amplification procedure is as follows: initial denaturation at 94° C. for 5 min; 30 cycles of denaturation at 94° C. for 30 s, annealing at 52° C. for 30 s, and extension at 72° C. for 90 s; and a final extension at 72° C. for 10 min.

In one embodiment of the invention, NEBuider recombination system is used to assemble the shuttle plasmid pXMJ19 and the NCg12176 or NCg12176$^{A528C}$ fragment with its own promoter to obtain an overexpression plasmid.

In one embodiment of the invention, the host strain is YP97158.

In one embodiment of the invention, the host strain is a strain carrying the polynucleotide sequence shown in SEQ ID NO: 2.

The recombinant strain obtained by the invention can be used alone to produce L-lysine by fermentation or can be mixed with other L-lysine-producing bacteria to produce L-lysine by fermentation.

In a further aspect, the invention provides a promoter nucleotide sequence, comprising the nucleotide sequence obtained by mutating the bases at positions −49, −51 and −54 to −58 in the promoter region shown in SEQ ID NO: 29.

According to the invention, the nucleotide at position −49 of the promoter region shown in SEQ ID NO: 29 is mutated from cytosine (C) to adenine (A), and the nucleotide at position −51 is mutated from guanine (G) to thymine (T), and the nucleotide sequence from positions −54 to −58 is mutated from CTGCA to GGTGT.

According to the invention, the promoter nucleotide sequence is as follows:

(a) the nucleotide sequence shown in SEQ ID NO: 30; or
(b) a nucleotide sequence having at least 90% identity, preferably at least 95% or at least 98% identity, to the nucleotide sequence shown in SEQ ID NO: 30 and retaining the enhancing activity of the promoter in (a), in which the nucleotide at position −49 is kept as adenine (A), the nucleotide at position −51 is kept as thymine (T), and the nucleotide sequence from positions −54 to −58 is kept as GGTGT.

The invention also provides an expression cassette comprising the above promoter, wherein the expression cassette comprises the promoter and a coding sequence operably linked to the promoter. In one embodiment of the invention, the coding sequence is the coding sequence of dapB gene.

The invention also provides a recombinant vector comprising the promoter nucleotide sequence of the invention.

According to the invention, the recombinant vector is constructed by ligating the promoter nucleotide sequence of the invention with a shuttle plasmid; in one embodiment of the invention, the shuttle plasmid is pK18mobsacB plasmid.

The invention also provides a recombinant strain containing the above promoter nucleotide sequence or the above recombinant vector.

According to the recombinant strain of the invention, it contains the nucleotide sequence shown in SEQ ID NO: 30. The nucleotide sequence shown in SEQ ID NO: 30 is the promoter region of dapB gene. Further, the nucleotide sequence shown in SEQ ID NO: 30 is linked to the dapB gene coding sequence. Specifically, the recombinant strain can contain the above-mentioned expression cassette or recombinant vector of the invention. Specifically, the recombinant strain of the invention is obtained by transforming an expression cassette or a recombinant vector. According to the recombinant strain of the invention, it is formed by introducing the mutated promoter nucleotide sequence into a host strain for recombination; the host strain can be selected from known L-lysine-producing strains in the art, for example, selected from at least one of Corynebacterium strains, the Corynebacterium strain can be Corynebacterium glutamicum, Brevibacterium flavum, Corynebacterium crenatum, Corynebacterium pekinense; preferably Corynebacterium glutamicum. In one embodiment of the invention, the host strain is YP97158.

According to the recombinant strain of the invention, pK18mobsacB plasmid is used as the vector.

According to the recombinant strain of the invention, it may further comprise other modifications.

The invention also provides a construction method of a L-lysine-producing recombinant strain, comprising the following steps:

(1) modifying the promoter region as shown in SEQ ID NO: 29 to mutate the bases at positions −49, −51 and −54 to −58, to obtain a nucleotide sequence comprising the mutated promoter region.

According to the invention, the mutation refers to that the nucleotide in position −49 of the promoter region shown in SEQ ID NO: 29 is mutated from cytosine (C) to adenine (A), and the nucleotide in position −51 is mutated from guanine (G) to thymine (T), the nucleotide sequence from positions −54 to −58 is mutated from CTGCA to GGTGT. Specifically, the nucleotide sequence of the mutated promoter region is shown in SEQ ID NO: 30. Further, the construction method also comprises the following steps:

(2) ligating the polynucleotide sequence of the mutated promoter region with a plasmid to construct a recombinant vector;
(3) introducing the recombinant vector into a host strain to obtain a L-lysine-producing recombinant strain containing the mutated promoter region.

According to the invention, in step (1), the mutation method includes mutagenesis, PCR site-directed mutagenesis or homologous recombination, preferably PCR site-directed mutagenesis.

According to the invention, step (1) comprises: designing two primer pairs for amplifying the promoter region of dapB gene, and then performing PCR to obtaining the nucleotide sequence of the mutated promoter region.

In one embodiment of the invention, the primers used in step (1) are as follows:

```
P1':
                                    (SEQ ID NO: 31)
5' CCGGAATTCACCATGCCGGACATGCGGAC3'(EcoR I)

P2':
                                    (SEQ ID NO: 32)
5' CCTTCTGAACGGGTTGTGGTATAATGGTGG 3'

P3':
                                    (SEQ ID NO: 33)
5' CCACCATTATACCACAACCCGTTCAGAAGG 3'

P4':
                                    (SEQ ID NO: 34)
5' ACATGCATGCGAATATTGACGTTGAGGAAG 3'(Sph I).
```

In one embodiment of the invention, step (1) comprises: using Corynebacterium glutamicum ATCC13032 as the template, performing PCR amplification with primers P1' and P2', P3' and P4', respectively, to obtain two DNA fragments containing point mutations; using the two DNA fragments as the template, performing overlap PCR amplification with primers P1' and P4', to obtain a DNA fragment comprising the nucleotide sequence (SEQ ID NO: 30) of the promoter region of the invention.

According to the invention, in step (1), through overlap PCR amplification, the two ends of the obtained DNA fragment contain EcoRI and Sph I restriction sites, respectively.

According to the invention, step (2) comprises: isolating and purifying the product amplified by the overlap PCR reaction, ligating the double-digested (by EcoR I/Sph I) fragment with the same double-digested (by EcoR I/Sph I) shuttle plasmid to obtain a recombinant vector by allelic substitution.

According to the invention, the shuttle plasmid is pK18mobsacB plasmid; the constructed recombinant vector is pK18-PdapB$^{(C(-49)A,G(-51)T, CTGCA(-54--58)GGTGT)}$.

In one embodiment of the invention, the recombinant plasmid has a kanamycin resistance marker.

In one embodiment of the invention, the transformation method in step (3) is electro-transformation method; exemplarily, in step (3), the recombinant plasmid is transformed into strain YP97158.

The invention also provides use of the aforementioned microorganism or recombinant strain of the invention in the preparation of L-lysine; or a method for increasing L-lysine fermentation yield; or a method for producing L-lysine.

According to the use and method of the invention, it comprises fermenting the microorganism or recombinant strain, and recovering L-lysine from the culture to prepare L-lysine. According to the use and method of the invention, the recombinant strain of the invention can be used alone or mixed with other L-lysine-producing bacteria.

The microorganism can be cultured in a suitable medium under culture conditions known in the art. The medium can contain: carbon sources, nitrogen sources, trace elements, and combinations thereof. During the culture process, the pH of the culture can be adjusted. In addition, during the culture process, the step of preventing the generation of air bubbles, for example, by using an antifoaming agent, may be included. In addition, during the culture process, the step of injecting gas into the culture may be included. The gas can include any gas capable of maintaining aerobic conditions of the culture. During the culture process, the temperature can be from 20° C. to 45° C. The resulting L-lysine can be recovered from the culture by treating the culture with sulfuric acid or hydrochloric acid and then a combination of methods such as anion exchange chromatography, concentration, crystallization and isoelectric precipitation can be performed.

In the invention,

```
SEQ ID NO 1: NCg12176 wild-type ORF sequence
ATGGCATTTGCAGACATTGTGCGCAGCGTCGAAAACCGCACCAACGCAG

CGACCCTCAACTGGTCCATCAAAAATGGCTGGAAGCCCGAAGTCACCGG

ATTTTCCGGGTACGGCTCCGGGCGTCGAGTGCGCGTCCTTGCGCGCGTG

CTCATGTCCAACCCCGAAAATTTGCTTGTCGACGCCCCCTCCCAATCAA

TTACCCAACAAGCACAGCGCGGTTGGCGCCAGTTCTTCACCATCCAAGT

GCCCAACCTGCCAGTAACTGTCACCGTTGGTGGGAAAACAGTTACCTCA

TCCACCAACGACAACGGCTACGTTGACCTCCTGGTGGAAGACCACAACC

TTGACCCCGGCTGGCACACCATCCAGATCCAAGCCGAAGGTTCCACCCC

CGCCGAAGCCGGCGTCCTCATCGTGGAAAACACCCCCCGAATCGGACTC

ATCTCCGACATCGACGACACCATCATGGTCACCTGGCTTCCCCGAGCAC

TGCTCGCCGCATGGAACTCGTGGGTTTTGCACACCAAAACCCGAAAACC

AGTCCCCGGAATGAACCGCTTCTACGAAGAACTCCTCAAAGACCACCCC

GACGCACCCGTGTTCTACCTCTCCACCGGCGCATGGAACACCTTTGAAA

CCCTCCAAGAGTTCATCAACAAACACGCACTCCCCGACGGCCCCATGCT

GCTCACCGACTGGGGACCAACCCCCACAGGACTATTCCGCTCAGGTCAA

GAGCACAAGAAAGTCCAACTGCGCAACCTGTTTATCGAATACCCCGACA

TGAAATGGATCCTCGTCGGCGACGATGGCCAACACGATCCCCTCATCTA

CGGCGAAGCAGTCGAAGAACACCCCAACCGCATCGCAGGCGTTGCAATC
```

```
CGTGAGCTCTCCCCCGGCGAACATGTGCTCTCCCACGGAACAACTGCGT

CACTGTCCACCATCACGACCAACGGGGGCCAAGGAGTCCCAGTAGTTCA

CGGCCGCGATGGATATGAGT TGCTGCAGCG CTACGAGACGAAGCCGT

TCG CCTGA
```

```
SEQ ID NO 2: NCg12176^{A528C} ORF sequence
ATGGCATTTGCAGACATTGTGCGCAGCGTCGAAAACCGCACCAACGCAG

CGACCCTCAACTGGTCCATCAAAAATGGCTGGAAGCCCGAAGTCACCGG

ATTTTCCGGGTACGGCTCCGGGCGTCGAGTGCGCGTCCTTGCGCGCGTG

CTCATGTCCAACCCCGAAAATTTGCTTGTCGACGCCCCCTCCCAATCAA

TTACCCAACAAGCACAGCGCGGTTGGCGCCAGTTCTTCACCATCCAAGT

GCCCAACCTGCCAGTAACTGTCACCGTTGGTGGGAAAACAGTTACCTCA

TCCACCAACGACAACGGCTACGTTGACCTCCTGGTGGAAGACCACAACC

TTGACCCCGGCTGGCACACCATCCAGATCCAAGCCGAAGGTTCCACCCC

CGCCGAAGCCCGCGTCCTCATCGTGGAAAACACCGCCCGAATCGGACTC

ATCTCCGACATCGACGACACCATCATGGTCACCTCGCTTCCCCGAGCAC

TCCTCGCCGCATGGAACTCGTGGGTTTTGCACACCAACACCCGAAAACC

AGTCCCCGAATGAACCGCTTCTACGAAGAACTCCTCAAAGACCACCCC

GACGCACCCGTGTTCTACCTCTCCACCGGCGCATGGAACACCTTTGAAA

CCCTCCAAGAGTTCATCAACAAACACGCACTCCCCGACGGCCCCATGCT

GCTCACCGACTGGGGACCAACCCCCACAGGACTATTCCGCTCAGGTCAA

GAGCACAAGAAAGTCCAACTGCGCAACCTGTTTATCGAATACCCCGACA

TGAAATGGATCCTCGTCGGCGACGATGGCCAACACGATCCCCTCATCTA

CGGCGAAGCAGTCGAAGAACACCCCAACCGCATCGCAGGCGTTGCAATC

CGTGAGCTCTCCCCCGGCGAACATGTGCTCTCCCACGGAACAACTGCGT

CACTGTCCACCATCACGACCAACGGGGGCCAAGGAGTCCCAGTAGTTCA

CGGCCGCGATGGATATGAGT TGCTGCAGCG CTACGAGACGAAGCCGT

TCG CCTGA
```

```
SEQ ID NO 3: amino acid sequence of the protein
encoded by wild-type NCg12176 gene
MAFADIVRSVENRTNAATLNWSIKNGWKPEVTGFSGYGSGRRVRVLARV

LMSNPENLLVDAPSQSITQQAQRGWRQFFTIQVPNLPVTVTVGGKTVTS

STNDNGYVDLLVEDHNLDPGWHTIQIQAEGSTPAEARVLIVENTARIGL

ISDIDDTIMVTWLPRALLAAWNSWVLHTKTRKPVPGMNRFYEELLKDHP

DAPVFYLSTGAWNTFETLQEFINKHALPDGPMLLTDWGPTPTGLFRSGQ

EHKKVQLRNLFIEYPDMKWILVGDDGQHDPLIYGEAVEEHPNRIAGVAI

RELSPGEHVLSHGTTA SLSTITTNGG QGVPVVHGRD GYELLQRYET

KPEA
```

```
SEQ ID NO 4: amino acid sequence of the protein
encoded by NCg12176^{K176N} gene
MAFADIVRSVENRTNAATLNWSIKNGWKPEVTGESGYGSGRRVRVLARV
```

-continued

LMSNPENLLVDAPSQSITQQAQRGWRQFFTIQVPNLPVTVTVGGKTVTS

STNDNGYVDLLVEDHNLDPGWHTIQIQAEGSTPARARVLIVENTARIGL

ISDIDDTIMVTWLPRALLAAWNSWVLHTNTRKPVPGMNRFYEELLKDHP

DAPVFYLSTGAWNTFETLQEFINKHALPDGPMLLTDWGPTPTGLERSGQ

EHKKVQLRNLFIEYPDMKWILVGDDGQHDPLIYGEAVEEHPNRIAGVAI

RELSPGEHVLSHGTTA SLSTITINGG QGVPVVHGRD GYELLQRYET

KPFA

SEQ ID NO 29: wild-type promoter sequence
cttaagtctc atatttcana catagttcca cctgtgtgat taatccctag aacggaacaaactgatgaac aatcgttaac aacacagacc aaaacggtca gttaggtatg gatatcagcaccttctgaac gggtacgtct agactggtgg gcgtttgaaa aactcttcgc cccacgaaaa tgaaggagca ta SEQ ID NO 29: mutated promoter sequence
cttaagtctc atatttcaaa catagttcca cctgtgtgat taatccctag aacggaacaaactgatgaac aatcgttaac aacacagacc aaaacggtca gttaggtatg gatatcagcaccttctgaac gggttgtggt ataatggtgg gcgtttgaaa aactcttcgc cccacgaaaa tgaaggagca ta In the invention, through performing down-regulation or knocking-out on the NCg12176 gene, it is found that the product encoded by the gene has an impact on the L-lysine production capacity, and by introducing a point mutation in the coding sequence, or increasing the copy number of the gene or overexpressing the gene, a recombinant strain is obtained, which is favorable for the production of high concentration of L-lysine compared with the unmodified strain.

In addition, a recombinant strain is obtained by introducing point mutations into the promoter region of dapB gene. Compared with the unmutated strain, the obtained strain also greatly increased the production of L-lysine, further improved the production efficiency, and reduced the production cost. Therefore, the invention is suitable for promotion and application.

DETAILED DESCRIPTION OF THE INVENTION

The technical solutions of the invention will be described in further detail below with reference to specific examples. It should be understood that the following examples are only for illustrating and explaining the invention, and should not be construed as limiting the protection scope of the invention. The technologies implemented based on the above content of the invention are all encompassed by the intended protection scope of the invention. Unless otherwise stated, the raw materials and reagents used in the following examples are all commercially available, or can be prepared by known methods; the operations performed are all known in the art, or are carried out according to the user manuals of commercially available products.

In the following examples, the compositions of the basic media used for culturing the strains are identical, and to this basic medium, correspondingly required sucrose, kanamycin or chloramphenicol, etc., can be added. The composition of the basic medium is as follows:

| Component | Formula |
| --- | --- |
| Sucrose | 10 g/L |
| Polypeptone | 10 g/L |
| Beef extract | 10 g/L |
| Yeast extract powder | 5 g/L |
| Urea | 2 g/L |
| NaCl | 2.5 g/L |
| Agar powder | 20 g/L |
| pH | 7.0 |
| Culture temperature | 32° C. |

The preparation and conditions of SSCP-PAGE in the following examples are as follows:

| Component | Amount (final concentration of acrylamide: 8%) |
| --- | --- |
| 40% Acrylamide | 8 ml |
| ddH$_2$O | 26 ml |
| Glycerin | 4 ml |
| 10*TBE | 2 ml |
| TEMED | 40 μl |
| 10% AP | 600 μl |
| Electrophoresis conditions | The electrophoresis tank is placed in ice and 1 × TBE buffer is used; voltage: 120 V; electrophoresis time: 10 h |

The fermentation medium formula and fermentation control process of L-Lysine in the following examples are as follows:

TABLE 1

| Fermentation medium formula | |
| --- | --- |
| Component | Formula |
| hydrolyzed sugar from starch | 30 g/L |
| (NH$_4$)$_2$SO$_4$ | 12 g/L |
| MgSO$_4$ | 0.87 g/L |
| Sirup | 20 g/L |
| Acidified corn pulp | 3 mL/L |
| H$_3$PO$_4$ | 0.4 mL/L |
| KCl | 0.53 g/L |
| Antifoaming agent (2% bubble enemy) | 4 mL/L |
| FeSO$_4$ | 120 mg/L |
| MnSO$_4$ | 120 mg/L |
| Nicotinamide | 42 mg/L |
| Calcium pantothenate | 6.3 mg/L |
| Vitamin B1 | 6.3 mg/L |
| Copper and zinc salt solution | 0.6 g/L |
| Biotin | 0.88 mg/L |

TABLE 2

| Fermentation control process | | | |
| --- | --- | --- | --- |
| Calibration | Temperature: 37° C., air volume: 4 L/min, speed: 1000 rpm, tank pressure: 0 mpa, calibrate after 5 min | | |
| Inoculum amount | 10% | Culture temperature (° C.) | 37° C. |
| pH | pH 6.9 ± 0.05 | Dissolved oxygen (DO) | 10-30% |
| Initial conditions | Temperature: 37° C., pH 6.9, tank pressure: 0 Mpa, air volume: 3 L/min, speed: 550 rpm | | |
| Whole | Whole process control: 1. when DO is less than 30%, | | |

TABLE 2-continued

| | Fermentation control process |
|---|---|
| process control | increase the speed by 750 rpm→800 rpm→air volume: 4 L/min→850 rpm→950 rpm; 2. at 6 hours of fermentation, increase tank pressure to 0.01 Mpa; at 12 h hours of fermentation, increase tank pressure by 0.02 Mpa→0.03 Mpa→0.04 Mpa→0.05 Mpa |
| Residual sugar control | 0.1-0.2% before F12 h; after F12 h, combined with DO requirement, residual sugar is controlled to be 0.1-0.05% |
| Ammonia-nitrogen control | 0.1-0.15 before F12 h; 0.15-0.25 for F12-F32 h; 0.1-0.15 after F32 h |
| Fed-batch materials | 25% Ammonia water, 70% concentrated sugar, 50% ammonium sulfate, 10% bubble enemy |
| Fermentation cycle | About 48 h |

Example 1: Construction of Transformation Vector pK18-NCg12176$^{A528C}$ Comprising Point-Mutated NCg12176 Gene Coding Region According to the genomic sequence of wild-type *Corynebacterium glutamicum* ATCC13032 published by NCBI, two primer pairs for amplifying NCg12176 gene coding region sequence were designed and synthesized, and a point mutation was introduced into the NCg12176 gene coding region (SEQ ID NO: 1) (the protein encoded by which has the amino acid sequence shown in SEQ ID NO: 3) of strain YP97158, which was deposited on Aug. 16, 2016 at China General Microbiological Culture Collection Center (Address: No. 1 West Beichen Road, Chaoyang District, Beijing, Telephone: 010-64807355) with a deposition number of CGMCC No. 12865 and has been recorded in Chinese Patent Application CN106367432A (Filing date: Sep. 1, 2016; Publication date: Feb. 1, 2017), by allelic substitution, such that the base at position 528 of the nucleotide sequence of the NCg12176 gene was changed from adenine (A) to cytosine (C) (SEQ ID NO: 2: NCg12176$^{A528C}$) and the amino acid residue at position 176 of the amino acid sequence of the corresponding encoded protein was changed from a lysine residue to an asparagine residue (SEQ ID NO: 4: NCg12176 K176N).

The primers designed were as follows (synthesized by Invitrogen, Shanghai):

```
P1:
                                      (SEQ ID NO: 5)
5' CAGTGCCAAGCTTGCATGCCTGCAGGTCGACTCTAGCGGCGAC
CGCATGGACACCG 3'

P2:
                                      (SEQ ID NO: 6)
5' CCGGGGACTGGTTTTCGGGTGTTGGTGTGC 3'

P3:
                                      (SEQ ID NO: 7)
5' GCACACCAACACCCGAAAACCAGTCCCCGG 3'

P4:
                                      (SEQ ID NO: 8)
5' CAGCTATGACCATGATTACGAATTCGAGCTCGGTACCCCGAGG
TCTCTCAGAATCGGT 3'
```

Construction method: using the genomic DNA of *Corynebacterium glutamicum* ATCC13032 as template, PCR amplifications were performed with primers P1 and P2, and primers P3 and P4, respectively.

PCR system: 10×Ex Taq Buffer 5 µL, dNTP Mixture (2.5 mM each) 4 µL, Mg$^{2+}$ (25 mM) 4 µL, primers (10 pM) 2 µL each, Ex Taq (5 U/µL) 0.25 µL, total volume 50 µL.

PCR amplification procedure: initial denaturation at 94° C. for 5 min; 30 cycles of denaturation at 94° C. for 30 s, annealing at 52° C. for 30 s, and extension at 72° C. for 40 s; and a final extension at 72° C. for 10 min. Two DNA fragments containing the NCg12176 gene coding region, NCg12176 Up and NCg12176 Down, with sizes of respectively 796 bp and 786 bp, were obtained.

The above two DNA fragments were isolated and purified by agarose gel electrophoresis and then using the two purified DNA fragments as template, overlap PCR amplification was performed with primers P1 and P4 to obtain a fragment of about 1552 bp.

PCR system: 10×Ex Taq Buffer 5 µL, dNTP Mixture (2.5 mM each) 4 µL, Mg$^{2+}$ (25 mM) 4 µL, primers (10 pM) 2 µL each, Ex Taq (5 U/µL) 0.25 µL, total volume 50 µL.

PCR amplification procedure: initial denaturation at 94° C. for 5 min; 30 cycles of denaturation at 94° C. for 30 s, annealing at 52° C. for 30 s, and extension at 72° C. for 90 s; and a final extension at 72° C. for 10 min.

This DNA fragment (NCg12176$^{A528C}$) caused the change of the base at position 528 of the NCg12176 gene coding region of YP97158 from adenine (A) to cytosine (C) and then the change of the amino acid residue at position 176 of the encoded protein from a lysine (K) residue to an asparagine (N) residue.

The pK18mobsacB plasmid (Addgene) was digested with Xba I. The NCg12176$^{A528C}$ and the linearized pK18mobsacB plasmid were isolated and purified by agarose gel electrophoresis, and then assembled by the NEBuider recombination system to obtain a vector pK18-NCg12176$^{A528C}$ containing a kanamycin resistance marker. The vector pK18-NCg12176$^{A528C}$ was sent for sequencing, and the correct vector pK18-NCg12176$^{A528C}$ containing point mutation (A-C) was stored for later use.

Example 2: Construction of Engineered Strain Containing Point-Mutated Gene NCg12176$^{A528C}$ Construction method: the plasmid pK18-NCg12176$^{A528C}$ for allelic substitution was transformed into L-lysine-producing strain YP97158 (see WO2014121669A1 for its construction method; it was confirmed by sequencing that wild-type NCg12176 gene coding region was retained on the chromosome of this strain) through electroporation; single colonies obtained after culture were identified by primer P1 and universal primer M13R respectively, and the strain from which a band of about 1559 bp could be amplified was a positive strain. The positive strain was cultured on the medium containing 15% sucrose, and single colonies obtained after culture were cultured on the medium containing kanamycin and without kanamycin at the same time; the strain that grew on the medium without kanamycin and did not grow on the medium containing kanamycin was further identified by PCR using the following primers (synthesized by Invitrogen, Shanghai):

```
P5:
                                      (SEQ ID NO: 9)
5' GAAAACACCGCCCGAATC 3'

P6:
                                      (SEQ ID NO: 10)
5' GGAGTGCGTGTTTGTTGATG 3'
```

The above PCR amplification product was subjected to sscp electrophoresis after high temperature denaturation and ice bath (the amplified fragment of plasmid pK18-

NCg12176$^{4528C}$ was used as a positive control, the amplified fragment of YP97158 was used as a negative control, and water was used as a blank control). Because of the different fragment structures, the fragments had different electrophoretic positions. The strain whose fragment had an electrophoretic position inconsistent with the negative control fragment, but the same as the positive control fragment had successful allelic substitution. PCR amplification was performed again with primers P5 and P6 to amplify the target fragment of the strain with successful allelic substitution, and the amplified fragment was ligated with the PMD19-T vector for sequencing. The strain with successful allelic substitution was verified by examining the mutated base sequence, and named as YPL-4-011.

Example 3: Construction of Engineered Strain Overexpressing NCg12176 or NCg12176$^{4528C}$ Gene on Genome According to the genomic sequence of wild-type *Corynebacterium glutamicum* ATCC13032 published by NCBI, three primer pairs for amplifying upstream and downstream homologous arm fragments and NCg12176 or NCg12176$^{4528C}$ gene coding region and promoter region sequence were designed and synthesized. The NCg12176 or NCg12176$^{4528C}$ gene was introduced into strain YP97158 by homologous recombination.

The primers designed were as follows (synthesized by Invitrogen, Shanghai):

```
P7:
                              (SEQ ID NO: 11)
5' CAGTGCCAAGCTTGCATGCCTGCAGGTCGACTCTAGAATGCGTT
CTGGACTGAGG 3'

P8:
                              (SEQ ID NO: 12)
5' AACACCATTGTCCCTGTTTTGGGCGAAATTTTCCCGGTGCACCGAG
AACAGATG 3'

P9:
                              (SEQ ID NO: 13)
5' CGGGAAAATTTCGCCCAAAACAGGGACAATGGTGTTATGGCATTTGC
AGACATTGTGCGC 3'

P10:
                              (SEQ ID NO: 14)
5' CTTGATTTAATTGCGC-
CATCTCAGGCGAACGGCTTCGTCTCGTAG 3'

P11:
                              (SEQ ID NO: 15)
5' CTACGAGACGAAGCCGTTCGCCTGAGATGGCGCAATTAAATCAAG 3'

P12:
                              (SEQ ID NO: 16)
5' CAGCTATGACCATGATTACGAATTCGAGCTCGGTACCCGCTATGACA
CCTTCAACGGATC 3'
```

Construction method: using the genomic DNA of *Corynebacterium glutamicum* ATCC13032 or YPL-4-011 as template, PCR amplifications were respectively carried out with primers P7 and P8, P9 and P10 and P11 and P12 to obtain the upstream homologous arm fragment of about 720 bp, NCg12176 gene and its promoter fragment of about 1092 bp, NCg12176$^{4528C}$ gene and its promoter fragment of about 1092 bp, and the downstream homologous arm fragment of about 653 bp. Using the mixture of above three fragments amplified (i.e., upstream homologous arm fragment, NCg12176 gene and its promoter fragment, downstream homologous arm fragment; or upstream homologous arm fragment, NCg12176$^{4528C}$ gene and its promoter fragment, downstream homologous arm fragment) as template, amplification was performed with primers P7 and P12 to obtain an integrating homologous arm fragment.

After the PCR reaction, the amplified products were recovered by electrophoresis, and the desired DNA fragments of about 2504 bp were recovered using a column gel DNA recovery kit (TIANGEN). The fragments were respectively ligated with Xba I-digested plasmid PK18mobsacB by NEBuider recombination system to obtain integrating plasmids PK18mobsacB-NCg12176 and PK18mobsacB-NCg12176$^{4528C}$. These two plasmids contained kanamycin resistance markers, and recombinants with the plasmids integrated into the genomes could be obtained by kanamycin resistance screening.

PCR system: 10×Ex Taq Buffer 5 μL, dNTP Mixture (2.5 mM each) 4 μL, Mg$^{2+}$ (25 mM) 4 μL, primers (10 pM) 2 μL each, Ex Taq (5 U/μL) 0.25 μL, total volume 50 μL.

PCR amplification procedure: initial denaturation at 94° C. for 5 min; 30 cycles of denaturation at 94° C. for 30 s, annealing at 52° C. for 30 s, and extension at 72° C. for 120 s; and a final extension at 72° C. for 10 min.

The two integrating plasmids were respectively electro-transformed into the L-lysine-producing strain YP97158, and single colonies obtained after culture were identified by PCR with primers P13 and P14. A fragment of about 1609 bp could be amplified from positive strains, and no fragment could be amplified from original strains. The positive strains were screened with 15% sucrose and cultured on media containing kanamycin and without kanamycin at the same time. The strain that grew in the medium without kanamycin and did not grow on the medium containing kanamycin was further identified by PCR using primers P15 and P16, and the strain from which a fragment of about 1123 bp could be amplified was a strain with YP97158 genome integrated with NCg12176 or NCg12176$^{4528C}$ gene, which were named as YPL-4-012 (without point mutation) and YPL-4-013 (with point mutation), respectively.

```
P13:
                              (SEQ ID NO: 17)
5' TCCAAGGAAGATACACGCC 3'

P14:
                              (SEQ ID NO: 18)
5' CCTGAGCGGAATAGTCCTGTG 3'

P15:
                              (SEQ ID NO: 19)
5' ACGCACCCGTGTTCTACCT 3'

P16:
                              (SEQ ID NO: 20)
5' CGTTGGAATCTTGCGTTG 3'
```

Example 4: Construction of Engineered Strain Overexpressing NCg12176 or NCg12176$^{4528C}$ Gene on Plasmid According to the genomic sequence of wild-type *Corynebacterium glutamicum* ATCC13032 published by NCBI, three primer pairs for amplifying NCg12176 or NCg12176$^{4528C}$ gene coding region and promoter region sequence were designed and synthesized. The primers designed were as follows (synthesized by Invitrogen, Shanghai):

P17:

(SEQ ID NO: 21)

5' GCTTGCATGCCTCCAGGTCGACTCTAGAGGATCCCCGGGAAAATTT
CGCCCAAAACAG 3'

P18:

(SEQ ID NO: 22)

5' ATCAGGCTGAAAATCTTCTCTCATCCGCCAAAACTCAGGCGAACGGC
TTCGTCTCGTAG 3'

Construction method: using the genomic DNA of wild-type *Corynebacterium glutamicum* ATCC13032 or YPL-4-011 as template, PCR amplifications were respectively carried out with primers P17 and P18 to obtain the NCgl2176 or NCgl2176$^{A528C}$ gene and its promoter fragment of about 1140 bp. The amplified products were recovered by electrophoresis, and the desired DNA fragments of about 1140 bp were recovered using a column gel DNA recovery kit (TIANGEN). The fragments were ligated with EcoR I-digested shuttle plasmid pXMJ19 by NEBuider recombination system to obtain overexpression plasmids pXMJ19-NCgl2176 and pXMJ19-NCgl2176$^{A528C}$, respectively. These two plasmids contained chloramphenicol resistance markers, and the strains transformed with the plasmids could be obtained by chloramphenicol resistance screening.

PCR system: 10×Ex Taq Buffer 5 µL, dNTP Mixture (2.5 mM each) 4 µL, Mg$^{2+}$ (25 mM) 4 µL, primers (10 pM) 2 µL each, Ex Taq (5 U/µL) 0.25 µL, total volume 50 µL.

PCR amplification procedure: initial denaturation at 94° C. for 5 min; 30 cycles of denaturation at 94° C. for 30 s, annealing at 52° C. for 30 s, and extension at 72° C. for 90 s; and a final extension at 72° C. for 10 min.

The plasmids were respectively electro-transformed into L-lysine-producing strain YP97158, and the single colonies obtained after culture were identified by PCR with primers M13R(−48) and P18. The strains from which a fragment of about 1147 bp could be amplified by PCR were the strains transformed with plasmids, which were named as YPL-4-014 (without point mutation) and YPL-4-015 (with point mutation), respectively.

Example 5: Construction of Engineered Strain Lacking NCgl2176 Gene on Genome According to the genomic sequence of *Corynebacterium glutamicum* ATCC13032 published by NCBI, two primer pairs for amplifying the fragments at the two ends of NCgl2176 gene coding region were synthesized and the PCR-amplified fragments were used as upstream and downstream homologous arm fragments. The primers designed were as follows (synthesized by Invitrogen, Shanghai):

P19:

(SEQ ID NO: 23)

5' CAGTGCCAAGCTTGCATGCCTGCAGGTCGACTCTAGTCAAAGAGGGC
GAGATAAT 3'

P20:

(SEQ ID NO: 24)

5' GTTCATGAGACACCCAGTAGGACGACCTACAGAATACTAGTCAGTG
3'

P21:

(SEQ ID NO: 25)

5' CACTGACTAGTATTCTGTAGGTCGTCCTACTGGGTGTCTCATGAAC
3'

P22:

(SEQ ID NO: 26)

5' CAGCTATGACCATGATTACGAATTCGAGCTCGGTACCCACCGCACGA
TGGTTCACT 3'

Using the genomic DNA of *Corynebacterium glutamicum* ATCC13032 as template, PCR amplification was carried out with primers P19 and P20, and P21 and P22 respectively to obtain an upstream homologous arm fragment of 852 bp and a downstream homologous arm fragment of 787 bp; and then overlap PCR was carried out with primers P19 and P22 to obtain an entire homologous arm fragment of 1639 bp. After the PCR reaction, the amplified product was recovered by electrophoresis, and the desired 1639 bp DNA fragment was recovered using a column gel DNA recovery kit (TIANGEN). The fragment was ligated with Xba I-digested shuttle plasmid pXMJ19 by NEBuider recombination system to obtain a knock-out plasmid. The plasmid contained a kanamycin resistance marker.

The knock-out plasmid was electro-transformed into lysine-producing strain YP97158, and single colonies obtained after culture were identified by PCR with the following primers (synthesized by Invitrogen, Shanghai):

P23:

(SEQ ID NO: 27)

5' TCAAAGAGGGCGAGATAAT 3'

P24:

(SEQ ID NO: 28)

5' ACCGCACGATGGTTCACT 3'

The strains from which 1521 bp and 2556 bp fragments could be amplified by the above PCR were positive strains, and the strains from which only a 2556 bp fragment could be amplified were the original strains. The positive strains were screened on 15% sucrose medium and cultured on the medium containing kanamycin and without kanamycin, respectively. The strain that grew in the medium without kanamycin and did not grow on the medium containing kanamycin was further identified by PCR with primers P23 and P24, and the strain from which a fragment of 1521 bp could be amplified was a genetically engineered strain with the NCgl2176 gene coding region knocked out, which was named as YPL-4-016.

Example 6: L-Lysine Fermentation Experiment

The strains constructed in Examples 2 to 5 and original strain YP97158 were fermented in the culture medium shown in Table 1 in the BLBIO-5GC-4-H model fermenter (purchased from Shanghai Bailun Biotechnology Co., Ltd.) according to the control process shown in Table 2 for fermentation experiments. The experiment for each strain was conducted in triplicate. The results are shown in Table 3.

TABLE 3

| L-Lysine fermentation experiment results | | |
|---|---|---|
| Strain | L-Lysine production (g/100 ml) | OD (660 nm) |
| YP97158 | 18.8 | 37.3 |
| YPL-4-011 | 19.0 | 37.2 |
| YPL-4-012 | 19.3 | 36.5 |

TABLE 3-continued

| | L-Lysine production (g/100 ml) | OD (660 nm) |
|---|---|---|
| Strain | | |
| YPL-4-013 | 19.8 | 37.0 |
| YPL-4-014 | 20.1 | 36.8 |
| YPL-4-015 | 20.3 | 35.9 |
| YPL-4-016 | 18.2 | 36.7 |

L-Lysine fermentation experiment results

The results are shown in Table 3. Overexpression of the NCg12176 gene, or point mutation in the NCg12176 gene coding region, i.e., NCg12176$^{A528C}$ and overexpression in *Corynebacterium glutamicum* contribute to the improvement of L-lysine production, while the gene down-regulation or knock-out is not conducive to the accumulation of lysine.

Example 7: Construction of Transformation Vector pK18-PdapB$^{(C(-49)A,\ G(-51)T,\ CTGCA(-54--58)GGTGT)}$ Comprising Point-Mutated dapB Gene Promoter Region According to the genomic sequence of wild-type *Corynebacterium glutamicum* ATCC13032 published by NCBI, two primer pairs for amplifying dapB gene promoter region sequence were designed and synthesized, and point mutations were introduced into the dapB gene promoter region (SEQ ID NO: 29) in strain YP97158 by allelic substitution, such that the nucleotide at position −49 of the nucleotide sequence of the dapB gene promoter region was mutated from cytosine (C) to adenine (A), the nucleotide at position −51 was mutated from guanine (G) to thymine (T), and the nucleotide sequence from positions −54 to −58 was mutated from CTGCA to GGTGT.

The primers designed were as follows (synthesized by Invitrogen, Shanghai):

```
P1':
                                        (SEQ ID NO: 31)
5' CCGGAATTCACCATGCCGGACATGCGGAC3' (EcoR I)

P2':
                                        (SEQ ID NO: 32)
5' CCTTCTGAACGGGTTGTGGTATAATGGTGG 3'

P3':
                                        (SEQ ID NO: 33)
5' CCACCATTATACCACAACCCGTTCAGAAGG 3'

P4':
                                        (SEQ ID NO: 34)
5' ACATGCATGCGAATATTGACGTTGAGGAAG 3' (Sph I).
```

Construction method: using the genomic DNA of *Corynebacterium glutamicum* ATCC13032 as template, PCR amplifications were performed with primers P1' and P2', and primers P3' and P4', respectively.

PCR system: 10×Ex Taq Buffer 5 µL, dNTP Mixture (2.5 mM each) 4 µL, Mg$^{2+}$ (25 mM) 4 µL, primers (10 pM) 2 µL each, Ex Taq (5 U/µL) 0.25 µL, total volume 50 µL.

PCR amplification procedure: initial denaturation at 94° C. for 5 min; 30 cycles of denaturation at 94° C. for 30 s, annealing at 52° C. for 30 s, and extension at 72° C. for 60 s; and a final extension at 72° C. for 10 min.

Two DNA fragments containing a point mutation, dapB Up and dapB Down, with sizes of respectively 665 bp and 664 bp were obtained. The above two DNA fragments were isolated and purified by agarose gel electrophoresis and then using the two purified DNA fragments as template, overlap PCR amplification was performed with primers P1' and P4' to obtain an Up-Down fragment of about 1279 bp.

Overlap PCR system: 10×Ex Taq Buffer 5 µL, dNTP Mixture (2.5 mM each) 4 µL, Mg$^{2+}$ (25 mM) 4 µL, primers (10 pM) 2 µL each, Ex Taq (5 U/µL) 0.25 µL, total volume 50 µL.

Overlap PCR amplification procedure: initial denaturation at 94° C. for 5 min; 30 cycles of denaturation at 94° C. for 30 s, annealing at 52° C. for 30 s, and extension at 72° C. for 90 s; and a final extension at 72° C. for 10 min.

This Up-Down fragment was isolated and purified by agarose gel electrophoresis. The fragment contained the dapB gene promoter region and its upstream and downstream sequences, and the two ends of the fragment contained EcoR I and Sph I restriction sites respectively. This DNA fragment resulted in the change of the nucleotide from C to A at position −49 of the YP97158 dapB gene promoter region, and the nucleotide from G to T at position −51, and the nucleotide sequence from CTGCA to GGTGT from positions −54 to −58.

The fragment was double-digested with restriction enzymes EcoR I and Sph I and then ligated with shuttle plasmid pK18mobsacB (Addgene) which was double-digested with the same restriction enzymes EcoR I and Sph I, to obtain allelic substitution plasmid pK18-PdapB$^{(C(-49)A,G(-51)T,\ CTGCA(-54--58)GGTGT)}$ containing a kanamycin resistance marker. The vector pK18-PdapB$^{(C(-49)A,G(-51)T,CTGCA(-54--58)GGTGT)}$ was sent for sequencing, and the correct vector pK18-PdapB$^{(C(-49)A,G(-51)T,CTGCA(-54--58)GGTGT)}$ containing point mutations was stored for later use.

Example 8: Construction of Engineered Strain Containing Point Mutated Vector pK18-PdapB$^{(C(-49)A,G(-51)T,CTGCA(-54--58)GGTGT)}$ Allelic substitution plasmid pK18-PdapB$^{(C(-49)A,G(-51)T,CTGCA(-54--58)GGTGT)}$ was electro-transformed into L-lysine-producing strain YP97158 (it was confirmed by sequencing that wild-type dapB gene promoter was retained on the chromosome of this strain), and single colonies obtained after culture were identified by primer P1' and universal primer M13R, respectively. A fragment of about 1350 bp could be amplified from positive strains. The positive strains were cultured on the medium containing 15% sucrose, and single colonies obtained after culture were cultured on the medium containing kanamycin and without kanamycin, respectively.

The strain that grew in the medium without kanamycin and did not grow on the medium containing kanamycin was further identified by PCR using the following primers (synthesized by Invitrogen, Shanghai):

```
P5':
                                        (SEQ ID NO: 35)
5' AGATCGTCGGACTCATTGAC 3'

P6':
                                        (SEQ ID NO: 36)
5' CAAACATAGTTCCACCTGTG 3'
```

The above PCR amplification product was subjected to sscp electrophoresis after high temperature denaturation and ice bath (the amplified fragment of plasmid pK18-PdapB$^{(C(-49)A,G(-51)T,CTCcA(-54--58)GGTT)}$ was used as a positive control, the amplified fragment of YP97158 was used as a negative control, and water was used as a blank control). Because of the different fragment structures, the fragments had different electrophoretic positions. The strain whose fragment had an electrophoretic position inconsistent with the negative control fragment, but the same as the positive control fragment had successful allelic substitution. PCR amplification was performed again to amplify the target fragment of the positive strain, and the amplified fragment was ligated with PMD19-T vector for sequencing. The strain with successful allelic substitution was verified by examining the mutated base sequence, and named as YPL-4-010.

Example 9: L-Lysine Fermentation Experiment

The strain YPL-4-010 constructed in Example 8 and original strain YP97158 were fermented in the culture medium shown in Table 1 in the BLBIO-5GC-4-H model fermenter (purchased from Shanghai Bailun Biotechnology Co., Ltd.) according to the control process shown in Table 2 for fermentation experiments. The experiment for each strain was conducted in triplicate. The results are shown in Table 4.

TABLE 4

L-Lysine fermentation experiment results

| Strain | | L-Lysine production (g/100 ml) | Conversion rate (%) |
|---|---|---|---|
| YP97158 | Batch 1 | 18.8 | 64..0 |
| | Batch 2 | 19.0 | 64.1 |

TABLE 4-continued

L-Lysine fermentation experiment results

| Strain | | L-Lysine production (g/100 ml) | Conversion rate (%) |
|---|---|---|---|
| | Batch 3 | 18.9 | 63.9 |
| | Mean | 18.9 | 64.0 |
| YPL-4-010 | Batch 1 | 20.8 | 64.6 |
| | Batch 2 | 20.6 | 64.6 |
| | Batch 3 | 20.9 | 64.5 |
| | Mean | 20.8 | 64.6 |
| Fold increase | | 10.05% | 0.94% |

Note: Conversion rate=(total mass of lysine/total consumption of glucose)×100%

The results are shown in Table 4, point mutation of the dapB gene promoter in *C. glutamicum*, $PdapB^{(C(-49)A, G(-51)}$ $T, CTGCA(-54--58)GGTGT)$, contributed to the improvement of L-lysine production.

The embodiments of the invention have been described above. However, the invention is not limited to the above-described embodiments. Any modification, equivalent replacement, improvement, etc. made within the spirit and principle of the invention shall be included within the protection scope of the invention.

The invention claimed is:

1. A method for producing L-lysine, comprising culturing a first recombinant strain contains a polynucleotide encoding a polypeptide that comprise an amino acid sequence of SEQ ID NO: 3, wherein the lysine residue at position 176 is substituted with an asparagine residue;

the polynucleotide sequence is formed by mutation of the base at position 528 of the polynucleotide sequence shown in SEQ ID NO: 1; and the mutation includes base mutation of adenine (A) to cytosine (C) at position 528 of the polynucleotide sequence shown in SEQ ID NO: 1;

or a second recombinant strain contains the promoter nucleotide sequence comprises the nucleotide sequence obtained by mutating the bases at positions −49, −51 and −54 to −58 in the promoter region shown in SEQ ID NO: 29;

or an expression cassette comprising the promoter nucleotide sequence comprises the nucleotide sequence obtained by mutating the bases at positions −49, −51 and −54 to −58 in the promoter region shown in SEQ ID NO: 29;

or a second recombinant vector comprises the promoter nucleotide sequence comprises the nucleotide sequence obtained by mutating the bases at positions −49, −51 and −54 to −58 in the promoter region shown in SEQ ID NO: 29;

wherein in the second recombinant strain or in the second recombinant vector or in the expression cassette, the nucleotide at position −49 of the promoter region shown in SEQ ID NO: 29 is mutated from cytosine (C) to adenine (A), the nucleotide at position −51 is mutated from guanine (G) to thymine (T), and the nucleotide sequence from positions −54 to −58 is mutated from CTGCA to GGTGT;

and both the first recombinant strain and the second recombinant strain use *Corynebacterium glutamicum* YP97158 as the host strain, and recovering L-lysine from the culture.

2. The method according to claim 1, wherein, the polynucleotide sequence comprises a polynucleotide encoding the amino acid sequence of SEQ ID NO: 4 or the polynucleotide sequence comprises the polynucleotide sequence shown in SEQ ID NO: 2.

3. The method according to claim 1, wherein in the expression cassette, a coding sequence operably linked to the promoter, or a coding sequence is the coding sequence of dapB gene.

4. The method according to claim 1, wherein the second recombinant vector is constructed by ligating the promoter nucleotide sequence with pK18mobsacB plasmid.

* * * * *

SEQUENCE LISTING

<160> NUMBER OF SEQ ID NOS: 36

<210> SEQ ID NO 1
<211> LENGTH: 1035
<212> TYPE: DNA
<213> ORGANISM: Corynebacterium glutamicum

<400> SEQUENCE: 1

```
atggcatttg cagacattgt gcgcagcgtc gaaaaccgca ccaacgcagc gaccctcaac      60
tggtccatca aaaatggctg gaagcccgaa gtcaccggat tttccgggta cggctccggg     120
cgtcgagtgc gcgtccttgc gcgcgtgctc atgtccaacc ccgaaaattt gcttgtcgac     180 gcccctccc aatcaattac ccaacaagca cagcgcggtt ggcgccagtt cttcaccatc      240
caagtgccca acctgccagt aactgtcacc gttggtggga aaacagttac ctcatccacc     300
aacgacaacg gctacgttga cctcctggtg gaagaccaca accttgaccc cggctggcac     360
accatccaga tccaagccga aggttccacc cccgccgaag cccgcgtcct catcgtggaa     420
aacaccgccc gaatcggact catctccgac atcgacgaca ccatcatggt cacctggctt     480
ccccgagcac tcctcgccgc atggaactcg tgggtttttgc acaccaaaac ccgaaaacca     540
gtccccggaa tgaaccgctt ctacgaagaa ctcctcaaag accaccccga cgcacccgtg     600
ttctacctct ccaccggcgc atggaacacc tttgaaaccc tccaagagtt catcaacaaa     660
cacgcactcc ccgacggccc catgctgctc accgactggg gaccaacccc cacaggacta     720
ttccgctcag gtcaagagca caagaaagtc caactgcgca acctgtttat cgaataccccc    780 gacatgaaat ggatcctcgt cggcgacgat ggccaacacg atccccctcat ctacggcgaa     840
```

-continued

```
gcagtcgaag aacaccccaa ccgcatcgca ggcgttgcaa tccgtgagct ctcccccggc      900
gaacatgtgc tctcccacgg aacaactgcg tcactgtcca ccatcacgac caacgggggc      960
caaggagtcc cagtagttca cggccgcgat ggatatgagt tgctgcagcg ctacgagacg     1020
aagccgttcg cctga                                                     1035
```

```
<210> SEQ ID NO 2
<211> LENGTH: 1035
<212> TYPE: DNA
<213> ORGANISM: Artificial Sequence
<220> FEATURE:
<223> OTHER INFORMATION: Synthesized

<400> SEQUENCE: 2
atggcatttg cagacattgt gcgcagcgtc gaaaaccgca ccaacgcagc gaccctcaac       60
tggtccatca aaaatggctg gaagcccgaa gtcaccggat tttccgggta cggctccggg      120
cgtcgagtgc gcgtccttgc gcgcgtgctc atgtccaacc ccgaaaattt gcttgtcgac      180
gccccctccc aatcaattac ccaacaagca cagcgcggtt ggcgccagtt cttcaccatc      240
caagtgccca acctgccagt aactgtcacc gttggtggga aaacagttac ctcatccacc      300
aacgacaacg gctacgttga cctcctggtg gaagaccaca accttgaccc cggctggcac      360
accatccaga tccaagccga aggttccacc cccgccgaag cccgcgtcct catcgtggaa      420
aacaccgccc gaatcggact catctccgac atcgacgaca ccatcatggt cacctggctt      480
ccccgagcac tcctcgccgc atggaactcg tgggtttttgc acaccaacac ccgaaaacca      540
gtccccggaa tgaaccgctt ctacgaagaa ctcctcaaag accaccccga cgcacccgtg      600
ttctacctct ccaccggcgc atggaacacc tttgaaaccc tccaagagtt catcaacaaa      660
cacgcactcc ccgacggccc catgctgctc accgactggg gaccaacccc cacaggacta      720
ttccgctcag gtcaagagca caagaaagtc caactgcgca acctgtttat cgaataccccc      780 gacatgaaat ggatcctcgt cggcgacgat ggccaacacg atccccctcat ctacggcgaa      840 gcagtcgaag aacaccccaa ccgcatcgca ggcgttgcaa tccgtgagct ctcccccggc      900
gaacatgtgc tctcccacgg aacaactgcg tcactgtcca ccatcacgac caacgggggc      960
caaggagtcc cagtagttca cggccgcgat ggatatgagt tgctgcagcg ctacgagacg     1020
aagccgttcg cctga                                                     1035
```

```
<210> SEQ ID NO 3
<211> LENGTH: 344
<212> TYPE: PRT
<213> ORGANISM: Corynebacterium glutamicum

<400> SEQUENCE: 3

Met Ala Phe Ala Asp Ile Val Arg Ser Val Glu Asn Arg Thr Asn Ala
1               5                   10                  15

Ala Thr Leu Asn Trp Ser Ile Lys Asn Gly Trp Lys Pro Glu Val Thr
            20                  25                  30

Gly Phe Ser Gly Tyr Gly Ser Gly Arg Arg Val Arg Val Leu Ala Arg
        35                  40                  45

Val Leu Met Ser Asn Pro Glu Asn Leu Leu Val Asp Ala Pro Ser Gln
    50                  55                  60

Ser Ile Thr Gln Gln Ala Gln Arg Gly Trp Arg Gln Phe Phe Thr Ile
65                  70                  75                  80

Gln Val Pro Asn Leu Pro Val Thr Val Thr Val Gly Gly Lys Thr Val
```

```
                        85              90              95

Thr Ser Ser Thr Asn Asp Asn Gly Tyr Val Asp Leu Leu Val Glu Asp
                100             105             110

His Asn Leu Asp Pro Gly Trp His Thr Ile Gln Ile Gln Ala Glu Gly
        115             120             125

Ser Thr Pro Ala Glu Ala Arg Val Leu Ile Val Glu Asn Thr Ala Arg
    130             135             140

Ile Gly Leu Ile Ser Asp Ile Asp Asp Thr Ile Met Val Thr Trp Leu
145             150             155             160

Pro Arg Ala Leu Leu Ala Ala Trp Asn Ser Trp Val Leu His Thr Lys
            165             170             175

Thr Arg Lys Pro Val Pro Gly Met Asn Arg Phe Tyr Glu Glu Leu Leu
        180             185             190

Lys Asp His Pro Asp Ala Pro Val Phe Tyr Leu Ser Thr Gly Ala Trp
        195             200             205

Asn Thr Phe Glu Thr Leu Gln Glu Phe Ile Asn Lys His Ala Leu Pro
    210             215             220

Asp Gly Pro Met Leu Leu Thr Asp Trp Gly Pro Thr Pro Thr Gly Leu
225             230             235             240

Phe Arg Ser Gly Gln Glu His Lys Lys Val Gln Leu Arg Asn Leu Phe
            245             250             255

Ile Glu Tyr Pro Asp Met Lys Trp Ile Leu Val Gly Asp Asp Gly Gln
        260             265             270

His Asp Pro Leu Ile Tyr Gly Glu Ala Val Glu Glu His Pro Asn Arg
        275             280             285

Ile Ala Gly Val Ala Ile Arg Glu Leu Ser Pro Gly Glu His Val Leu
    290             295             300

Ser His Gly Thr Thr Ala Ser Leu Ser Thr Ile Thr Thr Asn Gly Gly
305             310             315             320

Gln Gly Val Pro Val Val His Gly Arg Asp Gly Tyr Glu Leu Leu Gln
            325             330             335

Arg Tyr Glu Thr Lys Pro Phe Ala
            340
```

<210> SEQ ID NO 4
<211> LENGTH: 344
<212> TYPE: PRT
<213> ORGANISM: Artificial Sequence
<220> FEATURE:
<223> OTHER INFORMATION: Synthesized

<400> SEQUENCE: 4

```
Met Ala Phe Ala Asp Ile Val Arg Ser Val Glu Asn Arg Thr Asn Ala
1               5               10              15

Ala Thr Leu Asn Trp Ser Ile Lys Asn Gly Trp Lys Pro Glu Val Thr
            20              25              30

Gly Phe Ser Gly Tyr Gly Ser Gly Arg Arg Val Arg Val Leu Ala Arg
        35              40              45

Val Leu Met Ser Asn Pro Glu Asn Leu Leu Val Asp Ala Pro Ser Gln
    50              55              60

Ser Ile Thr Gln Gln Ala Gln Arg Gly Trp Arg Gln Phe Phe Thr Ile
65              70              75              80

Gln Val Pro Asn Leu Pro Val Thr Val Thr Val Gly Gly Lys Thr Val
            85              90              95

Thr Ser Ser Thr Asn Asp Asn Gly Tyr Val Asp Leu Leu Val Glu Asp
```

-continued

```
              100               105               110

His Asn Leu Asp Pro Gly Trp His Thr Ile Gln Ile Gln Ala Glu Gly
            115               120               125

Ser Thr Pro Ala Glu Ala Arg Val Leu Ile Val Glu Asn Thr Ala Arg
    130               135               140

Ile Gly Leu Ile Ser Asp Ile Asp Asp Thr Ile Met Val Thr Trp Leu
145               150               155               160

Pro Arg Ala Leu Leu Ala Ala Trp Asn Ser Trp Val Leu His Thr Asn
                165               170               175

Thr Arg Lys Pro Val Pro Gly Met Asn Arg Phe Tyr Glu Glu Leu Leu
            180               185               190

Lys Asp His Pro Asp Ala Pro Val Phe Tyr Leu Ser Thr Gly Ala Trp
            195               200               205

Asn Thr Phe Glu Thr Leu Gln Glu Phe Ile Asn Lys His Ala Leu Pro
    210               215               220

Asp Gly Pro Met Leu Leu Thr Asp Trp Gly Pro Thr Pro Thr Gly Leu
225               230               235               240

Phe Arg Ser Gly Gln Glu His Lys Lys Val Gln Leu Arg Asn Leu Phe
                245               250               255

Ile Glu Tyr Pro Asp Met Lys Trp Ile Leu Val Gly Asp Asp Gly Gln
            260               265               270

His Asp Pro Leu Ile Tyr Gly Glu Ala Val Glu Glu His Pro Asn Arg
            275               280               285

Ile Ala Gly Val Ala Ile Arg Glu Leu Ser Pro Gly Glu His Val Leu
    290               295               300

Ser His Gly Thr Thr Ala Ser Leu Ser Thr Ile Thr Thr Asn Gly Gly
305               310               315               320

Gln Gly Val Pro Val Val His Gly Arg Asp Gly Tyr Glu Leu Leu Gln
                325               330               335

Arg Tyr Glu Thr Lys Pro Phe Ala
            340
```

<210> SEQ ID NO 5
<211> LENGTH: 56
<212> TYPE: DNA
<213> ORGANISM: Artificial Sequence
<220> FEATURE:
<223> OTHER INFORMATION: Synthesized

<400> SEQUENCE: 5
cagtgccaag cttgcatgcc tgcaggtcga ctctagcggc gaccgcatgg acaccg          56

<210> SEQ ID NO 6
<211> LENGTH: 30
<212> TYPE: DNA
<213> ORGANISM: Artificial Sequence
<220> FEATURE:
<223> OTHER INFORMATION: Synthesized

<400> SEQUENCE: 6
ccggggactg gttttcgggt gttggtgtgc          30

<210> SEQ ID NO 7
<211> LENGTH: 30
<212> TYPE: DNA
<213> ORGANISM: Artificial Sequence
<220> FEATURE:
<223> OTHER INFORMATION: Synthesized -continued

```
<400> SEQUENCE: 7
gcacaccaac acccgaaaac cagtccccgg                                          30

<210> SEQ ID NO 8
<211> LENGTH: 58
<212> TYPE: DNA
<213> ORGANISM: Artificial Sequence
<220> FEATURE:
<223> OTHER INFORMATION: Synthesized

<400> SEQUENCE: 8
cagctatgac catgattacg aattcgagct cggtacccg aggtctctca gaatcggt         58

<210> SEQ ID NO 9
<211> LENGTH: 18
<212> TYPE: DNA
<213> ORGANISM: Artificial Sequence
<220> FEATURE:
<223> OTHER INFORMATION: Synthesized

<400> SEQUENCE: 9
gaaaacaccg cccgaatc                                                      18

<210> SEQ ID NO 10
<211> LENGTH: 20
<212> TYPE: DNA
<213> ORGANISM: Artificial Sequence
<220> FEATURE:
<223> OTHER INFORMATION: Synthesized

<400> SEQUENCE: 10
ggagtgcgtg tttgttgatg                                                    20

<210> SEQ ID NO 11
<211> LENGTH: 55
<212> TYPE: DNA
<213> ORGANISM: Artificial Sequence
<220> FEATURE:
<223> OTHER INFORMATION: Synthesized

<400> SEQUENCE: 11
cagtgccaag cttgcatgcc tgcaggtcga ctctagaatg cgttctggac tgagg          55

<210> SEQ ID NO 12
<211> LENGTH: 54
<212> TYPE: DNA
<213> ORGANISM: Artificial Sequence
<220> FEATURE:
<223> OTHER INFORMATION: Synthesized

<400> SEQUENCE: 12
aacaccattg tccctgtttt gggcgaaatt ttcccggtgc accgagaaca gatg           54

<210> SEQ ID NO 13
<211> LENGTH: 60
<212> TYPE: DNA
<213> ORGANISM: Artificial Sequence
<220> FEATURE:
<223> OTHER INFORMATION: Synthesized

<400> SEQUENCE: 13
cgggaaaatt tcgcccaaaa cagggacaat ggtgttatgg catttgcaga cattgtgcgc    60

<210> SEQ ID NO 14
<211> LENGTH: 45
```

```
<212> TYPE: DNA
<213> ORGANISM: Artificial Sequence
<220> FEATURE:
<223> OTHER INFORMATION: Synthesized

<400> SEQUENCE: 14
cttgatttaa ttgcgccatc tcaggcgaac ggcttcgtct cgtag                45

<210> SEQ ID NO 15
<211> LENGTH: 45
<212> TYPE: DNA
<213> ORGANISM: Artificial Sequence
<220> FEATURE:
<223> OTHER INFORMATION: Synthesized

<400> SEQUENCE: 15
ctacgagacg aagccgttcg cctgagatgg cgcaattaaa tcaag                45

<210> SEQ ID NO 16
<211> LENGTH: 60
<212> TYPE: DNA
<213> ORGANISM: Artificial Sequence
<220> FEATURE:
<223> OTHER INFORMATION: Synthesized

<400> SEQUENCE: 16
cagctatgac catgattacg aattcgagct cggtacccgc tatgacacct tcaacggatc   60

<210> SEQ ID NO 17
<211> LENGTH: 19
<212> TYPE: DNA
<213> ORGANISM: Artificial Sequence
<220> FEATURE:
<223> OTHER INFORMATION: Synthesized

<400> SEQUENCE: 17
tccaaggaag atacacgcc                                             19

<210> SEQ ID NO 18
<211> LENGTH: 21
<212> TYPE: DNA
<213> ORGANISM: Artificial Sequence
<220> FEATURE:
<223> OTHER INFORMATION: Synthesized

<400> SEQUENCE: 18
cctgagcgga atagtcctgt g                                          21

<210> SEQ ID NO 19
<211> LENGTH: 19
<212> TYPE: DNA
<213> ORGANISM: Artificial Sequence
<220> FEATURE:
<223> OTHER INFORMATION: Synthesized

<400> SEQUENCE: 19
acgcacccgt gttctacct                                             19

<210> SEQ ID NO 20
<211> LENGTH: 18
<212> TYPE: DNA
<213> ORGANISM: Artificial Sequence
<220> FEATURE:
<223> OTHER INFORMATION: Synthesized

<400> SEQUENCE: 20
```

-continued cgttggaatc ttgcgttg                                                                        18

<210> SEQ ID NO 21
<211> LENGTH: 59
<212> TYPE: DNA
<213> ORGANISM: Artificial Sequence
<220> FEATURE:
<223> OTHER INFORMATION: Synthesized

<400> SEQUENCE: 21
gcttgcatgc ctgcaggtcg actctagagg atcccccggg aaaatttcgc ccaaaacag        59

<210> SEQ ID NO 22
<211> LENGTH: 59
<212> TYPE: DNA
<213> ORGANISM: Artificial Sequence
<220> FEATURE:
<223> OTHER INFORMATION: Synthesized

<400> SEQUENCE: 22
atcaggctga aaatcttctc tcatccgcca aaactcaggc gaacggcttc gtctcgtag        59

<210> SEQ ID NO 23
<211> LENGTH: 55
<212> TYPE: DNA
<213> ORGANISM: Artificial Sequence
<220> FEATURE:
<223> OTHER INFORMATION: Synthesized

<400> SEQUENCE: 23
cagtgccaag cttgcatgcc tgcaggtcga ctctagtcaa agagggcgag ataat        55

<210> SEQ ID NO 24
<211> LENGTH: 46
<212> TYPE: DNA
<213> ORGANISM: Artificial Sequence
<220> FEATURE:
<223> OTHER INFORMATION: Synthesized

<400> SEQUENCE: 24
gttcatgaga cacccagtag gacgacctac agaatactag tcagtg        46

<210> SEQ ID NO 25
<211> LENGTH: 46
<212> TYPE: DNA
<213> ORGANISM: Artificial Sequence
<220> FEATURE:
<223> OTHER INFORMATION: Synthesized

<400> SEQUENCE: 25
cactgactag tattctgtag gtcgtcctac tgggtgtctc atgaac        46

<210> SEQ ID NO 26
<211> LENGTH: 56
<212> TYPE: DNA
<213> ORGANISM: Artificial Sequence
<220> FEATURE:
<223> OTHER INFORMATION: Synthesized

<400> SEQUENCE: 26
cagctatgac catgattacg aattcgagct cggtacccac cgcacgatgg ttcact        56

<210> SEQ ID NO 27
<211> LENGTH: 19
<212> TYPE: DNA
<213> ORGANISM: Artificial Sequence -continued

```
<220> FEATURE:
<223> OTHER INFORMATION: Synthesized

<400> SEQUENCE: 27
tcaaagaggg cgagataat                                                    19

<210> SEQ ID NO 28
<211> LENGTH: 18
<212> TYPE: DNA
<213> ORGANISM: Artificial Sequence
<220> FEATURE:
<223> OTHER INFORMATION: Synthesized

<400> SEQUENCE: 28
accgcacgat ggttcact                                                     18

<210> SEQ ID NO 29
<211> LENGTH: 192
<212> TYPE: DNA
<213> ORGANISM: Corynebacterium glutamicum

<400> SEQUENCE: 29
cttaagtctc atatttcaaa catagttcca cctgtgtgat taatccctag aacggaacaa      60
actgatgaac aatcgttaac aacacagacc aaaacggtca gttaggtatg gatatcagca     120
ccttctgaac gggtacgtct agactggtgg gcgtttgaaa aactcttcgc cccacgaaaa     180
tgaaggagca ta                                                         192

<210> SEQ ID NO 30
<211> LENGTH: 192
<212> TYPE: DNA
<213> ORGANISM: Artificial Sequence
<220> FEATURE:
<223> OTHER INFORMATION: Synthesized

<400> SEQUENCE: 30
cttaagtctc atatttcaaa catagttcca cctgtgtgat taatccctag aacggaacaa      60
actgatgaac aatcgttaac aacacagacc aaaacggtca gttaggtatg gatatcagca     120
ccttctgaac gggttgtggt ataatggtgg gcgtttgaaa aactcttcgc cccacgaaaa     180
tgaaggagca ta                                                         192

<210> SEQ ID NO 31
<211> LENGTH: 29
<212> TYPE: DNA
<213> ORGANISM: Artificial Sequence
<220> FEATURE:
<223> OTHER INFORMATION: Synthesized

<400> SEQUENCE: 31
ccggaattca ccatgccgga catgcggac                                        29

<210> SEQ ID NO 32
<211> LENGTH: 30
<212> TYPE: DNA
<213> ORGANISM: Artificial Sequence
<220> FEATURE:
<223> OTHER INFORMATION: Synthesized

<400> SEQUENCE: 32
ccttctgaac gggttgtggt ataatggtgg                                       30

<210> SEQ ID NO 33
```

-continued

```
<211> LENGTH: 30
<212> TYPE: DNA
<213> ORGANISM: Artificial Sequence
<220> FEATURE:
<223> OTHER INFORMATION: Synthesized

<400> SEQUENCE: 33
ccaccattat accacaaccc gttcagaagg                                      30

<210> SEQ ID NO 34
<211> LENGTH: 30
<212> TYPE: DNA
<213> ORGANISM: Artificial Sequence
<220> FEATURE:
<223> OTHER INFORMATION: Synthesized

<400> SEQUENCE: 34
acatgcatgc gaatattgac gttgaggaag                                      30

<210> SEQ ID NO 35
<211> LENGTH: 20
<212> TYPE: DNA
<213> ORGANISM: Artificial Sequence
<220> FEATURE:
<223> OTHER INFORMATION: Synthesized

<400> SEQUENCE: 35
agatcgtcgg actcattgac                                                 20

<210> SEQ ID NO 36
<211> LENGTH: 20
<212> TYPE: DNA
<213> ORGANISM: Artificial Sequence
<220> FEATURE:
<223> OTHER INFORMATION: Synthesized

<400> SEQUENCE: 36
caaacatagt tccacctgtg                                                 20
```